(12) United States Patent
Okoli et al.

(10) Patent No.: US 10,386,305 B2
(45) Date of Patent: Aug. 20, 2019

(54) TRIBOLUMINESCENT OPTICAL FIBER SENSING PATCH

(71) Applicant: Florida State University Research Foundation, Inc., Tallahassee, FL (US)

(72) Inventors: Okenwa Okoli, Tallahassee, FL (US); David Olawale, Tallahassee, FL (US)

(73) Assignee: The Florida State University Research Foundation, Inc., Tallahassee, FL (US)

( * ) Notice: Subject to any disclaimer, the term of this patent is extended or adjusted under 35 U.S.C. 154(b) by 133 days.

(21) Appl. No.: 15/596,913

(22) Filed: May 16, 2017

(65) Prior Publication Data

US 2017/0328741 A1 Nov. 16, 2017

Related U.S. Application Data

(60) Provisional application No. 62/337,060, filed on May 16, 2016.

(51) Int. Cl.
*G01N 21/70* (2006.01)
*G02B 6/036* (2006.01)
*G01M 5/00* (2006.01)
*G01L 1/24* (2006.01)

(52) U.S. Cl.
CPC ............. *G01N 21/70* (2013.01); *G01L 1/242* (2013.01); *G01M 5/0016* (2013.01); *G01M 5/0041* (2013.01); *G01M 5/0091* (2013.01); *G02B 6/03694* (2013.01)

(58) Field of Classification Search
CPC ........................................................ G01L 1/25
See application file for complete search history.

(56) References Cited

U.S. PATENT DOCUMENTS 5,905,260 A * 5/1999 Sage .................. G01L 1/24
250/307
7,307,702 B1 * 12/2007 Mathur .................. G01L 1/24
356/32

* cited by examiner

*Primary Examiner* — Tony Ko
(74) *Attorney, Agent, or Firm* — Eversheds Sutherland (US) LLP

(57) ABSTRACT

A sensor that can be used for real time monitoring of load and structural health in engineering structures is provided. The sensor may include a patch with a portion of an optical fiber embedded therein. There may also be triboluminescent materials dispersed within the patch, on and/or near the portions of the optical fiber embedded in the patch. There may be micro-excitors located in proximity to the triboluminescent materials and on the surface of the optical fiber. Loading events and/or damage to the monitored structure may result in a triboluminescent emission from the triboluminescent material that can be guided via the optical fiber. Analysis of the triboluminescent emission may provide information on the magnitude of the applied load as well as the occurrence, severity and location of damage in the structure.

20 Claims, 10 Drawing Sheets

TRIBOLUMINESCENT OPTICAL FIBER SENSING PATCH

CROSS-REFERENCE TO RELATED APPLICATIONS

This application claims the benefit of priority to U.S. Provisional Patent Application No. 62/337,060, filed on May 16, 2016, which is hereby incorporated herein by reference in its entirety.

STATEMENT REGARDING FEDERALLY SPONSORED RESEARCH OR DEVELOPMENT

This invention was made with government support under grant number CMMI0969413 awarded by the National Science Foundation. The government has certain rights in the invention.

FIELD OF THE INVENTION

This invention generally relates to sensors, and more particularly to triboluminescent optical fiber sensors.

BACKGROUND OF THE INVENTION

Fiber reinforced polymer (FRP) composites continue to find increasing use in structural applications, for example in the aerospace and marine industries, as well as in wind turbine blades and civil infrastructural systems. The increasing use of fiber reinforced polymer composites has largely been enabled by their relatively high strength to weight ratios, and excellent fatigue and corrosion resistance.

BRIEF DESCRIPTION OF THE FIGURES

Reference will now be made to the accompanying figures, which are not necessarily drawn to scale, and wherein.

DETAILED DESCRIPTION

Figure 1:
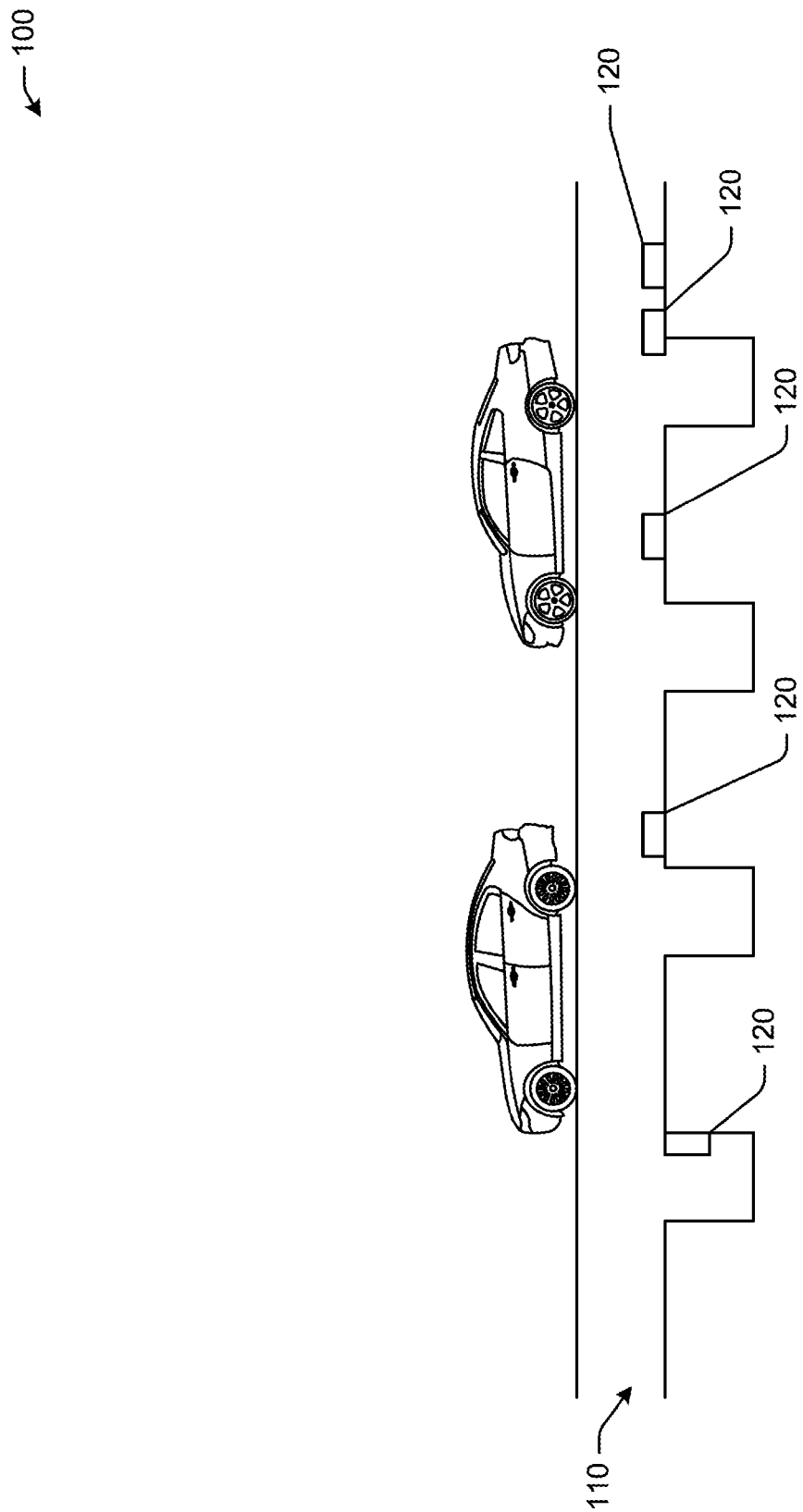
FIG. 1 is a schematic diagram illustrating an example physical infrastructure with triboluminescent patch sensors provided, in accordance with embodiments of the disclosure.

Embodiments of the disclosure are described more fully hereinafter with reference to the accompanying drawings, in which embodiments of the invention are shown. This disclosure may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

Embodiments of the disclosure may provide systems, apparatuses, and methods for in-situ monitoring of load and structural health of structural materials, such as composite materials. In some embodiments, these systems, apparatuses, and methods may enable continuous monitoring of a structure (e.g., wind turbines blades, bridges, builds, etc.) distributed over the structure to be monitored. In example embodiments, triboluminescent optical fiber sensing patch ("ITOFPress") or triboluminescent patch sensors may be used for monitoring load and structural health. The patch sensors, as disclosed herein, may provide an ability to monitor structures without changing the composition, mechanical properties, and thermal properties of the monitored material. In example embodiments, the patch sensors may provide a relatively high signal to noise ratio ("SNR") of signals indicative of pressure (e.g., load) or fracture from the monitoring. The patch sensors, as described herein, may be provided on a surface of a structure being monitored, and as a result, may not need to be embedded within the monitored material. As a result, the structure to be monitored may be provided with the patch sensors at any time (e.g., prior to deployment, after a certain number of hours/days of operation, etc.). Additionally, by not having to embed sensors within materials, the microscopic and/or macroscopic properties of the material may not be altered for the purposes of load and structural monitoring.

FRP materials are used in a wide variety of applications, such as wind turbines. They are, however, susceptible to low velocity impact resulting in barely visible impact damage (BVID). In particular, as wind blades become larger and are located farther away from the shore, there may be a growing need to monitor and control the various loads acting on them. The wind blades are the source of the most significant loads on the turbine and the ability to reduce the loads on the blades may result in the reduction of the loads throughout the drivetrain and tower. Wind turbines require control to ensure safe operation of the turbine, to maximize power production, and to minimize extreme and fatigue loading of the structure. The ITOFPress Sensor, as disclosed herein, may provide quasi-distributed load information along the length of a wind blade as inputs for enhanced active control of wind turbines and also for damage monitoring. One key advantage of the ITOFPress Sensor over other sensors is that it does not require an external power source at the sensing location, nor does it require any for signal transmission along the length of the blade to the location of the local processor, such as a processor located in a nacelle of a wind turbine.

In example embodiments, the patch sensor may include triboluminescent materials therein. Triboluminescence (TL) is the emission of light from materials when stressed, pulled apart, ripped, scratched, rubbed, or fractured. In example embodiments, the patch sensor may include one or more optical fibers (e.g., without any jacket) encapsulated within the material of the shape of the patch. Triboluminescent material may be provided on the optical fiber embedded within the patch portion and/or on the patch portion. Micro-excitors (e.g., abrasives/abrasive particles) may be positioned in relative proximity to, such as in contact with, a triboluminescent material coated optical fiber of the patch sensor. This patch portion, within which the optical fiber is embedded, may have material properties such that a sufficient amount of force may be imparted thereto from a structure to be monitored, such that the force may produce a light emitting event at the triboluminescent crystals provided on or near the optical fiber. The patch portion may also permit the relative motion (e.g., rubbing) of the micro-excitors and the triboluminescent optical fiber for TL emission during loading of the structure. In one sense, the micro-excitors may concentrate and/or amplify the tribological effects of any forces imparted to the patch of the patch sensor, such as compressive, tensile, shear, or indeed, any other forces. The micro-excitors may be positioned on or adhered to a different material from the patch material to enhance the relative (gliding/sliding) motion while giving the patch the desired shape (curved, bent, etc). The patch portion may be fabricated using any suitable material, such as any variety of polymers, polyethylene, epoxies, or the like. In some cases, the material selected for the patch may have an index of refraction such that any light emitted by triboluminescent materials embedded therein may be guided (e.g., total internal reflection of the wavelengths emitted by the triboluminescent materials). Thus, the light emitted by the triboluminescent materials during an emitting event may be received by one or more of the optical fibers of the patch sensor, and may be transmitted by one or more of the optical fibers to, for example, a photodetector.

In some example embodiments, the patch sensor may be fabricated by the optical fiber being embedded within polymer material using any suitable mechanism, such as lamination, molding, epoxy cure, etc. The outsides of the patch sensor may be made opaque to reject any outside light from entering the optical fiber. In example embodiments, paints or pigments may be provided to the outside of the polymer portions of the patch to darken the outside to prevent incursion of outside light.

In example embodiments, an uncovered (e.g., without a jacket portion) portion of optical fiber may be looped and attached to a bottom substrate, such as with epoxy or by impregnation where the bottom substrate may be relatively soft. The bottom substrate may be a polymer material, such as a sheet of polyethylene. A portion of the optical fiber that is not attached to the bottom substrate may have a jacket thereon (e.g., over the cladding of the optical fiber). Next, one or more different types of triboluminescent materials may be provided on and/or around the portion of the optical fiber attached to the bottom substrate. After the triboluminescent material is provided on or near the optical fiber, the fiber may be encapsulated with additional polymer. This may be performed by laminating a sheet of polymer over the bottom substrate and/or depositing (e.g., coating, spray dispense, etc.) epoxy that may be cured (e.g., thermal cure, UV cure, etc.). In example embodiments, the sensor may be fabricated in a single process in which a polymer system is casted over a triboluminescent coated optical fiber with micro-excitors arranged in a mold. After encapsulating the optical fiber loop, the outside of the encapsulating polymer materials may be made opaque, such as by providing darkening materials and/or reflective materials thereon. Epoxy or tape may be provided on the patch sensor to attach it to the material and/or structure that is to be monitored for structural and/or mechanical events. In example embodiments, the epoxy or tape used to affix the sensing patch to the structure to be monitored may have sufficient adhesion and rigidity to transfer any forces in the underlying structure to be monitored to the sensing patch, such that the forces result in a suitable tribological event to cause light emission from the TL sensors.

Example embodiments of the invention will now be described with reference to the accompanying figures.

Referring now to FIG. 1, an example physical infrastructure 100 is shown, in the form of a bridge 110, with triboluminescent patch sensors 120 provided thereon, in accordance with embodiments of the disclosure. The triboluminescent patch sensors 120 may be provided on any suitable surfaces of the bridge 110 in locations where there may be relatively higher probability of damage and/or cracking. For example, one or more triboluminescent patch sensors 120 may be provided near the joining portion of the bridge 110 deck and the bridge 110 foundation. In this case, the triboluminescent patch sensors 120 may be affixed on concrete, cement, rebar, or other materials used in the construction of the bridge 110. Sufficiently strong forces in the bridge 110 in relative proximity to a triboluminescent patch sensor 120 may impart enough of a force to the triboluminescent patch sensor 120 to result in a tribological emission event by the triboluminescent crystals of the triboluminescent patch sensor 120. That emission event then may be detected by an optical detection device, such as an optical detection device or photodetector, which may be coupled to a computer for logging the emission events.

An application of triboluminescent optical fiber sensors 120 may be the monitoring of FRP and repair systems in concrete structures such as bridges 110. There are over 600,000 bridges in the United States of America, and an estimated 25 percent of these are in need of repairs. Thus, this sector is in need of structural monitoring systems such as the triboluminescent patch sensors 120 as described herein. Furthermore, the triboluminescent patch sensors 120 may be used for FRP to act as an impact sensor system to monitor impact to structures like bridges over time. Such information may be used in assessing the structural state of the structure, such as the bridge 110, thereby enabling timely repair and prevention of catastrophic failures. The triboluminescent patch sensors 120 enable the application of triboluminescence sensing to concrete or cementitious composites. The triboluminescent patch sensors 120 provided on concrete, for example, can produce a cementitious composite with in-situ damage detection capability, such as crack detection capability.

Figure 2:
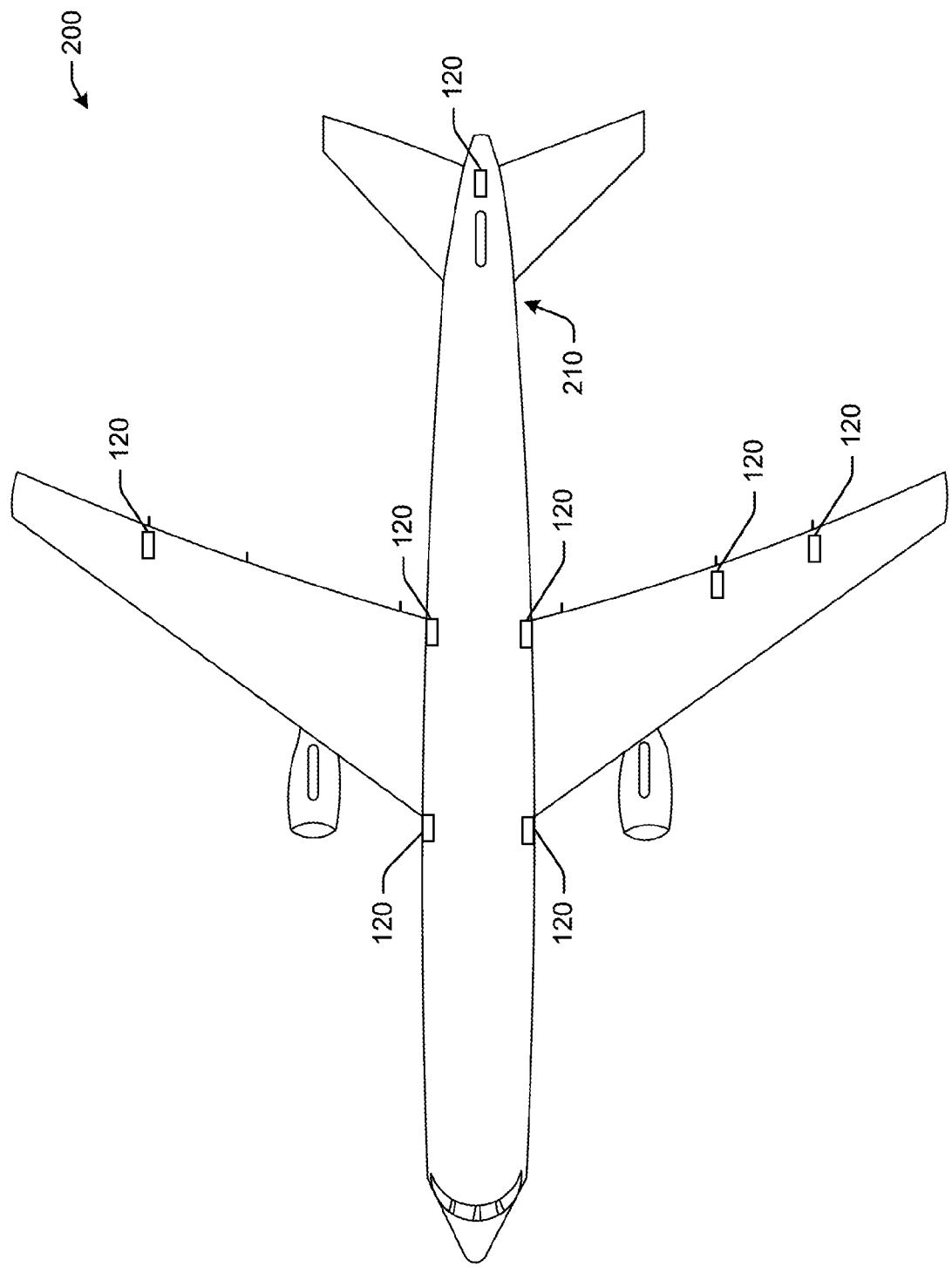
FIG. 2 is a schematic diagram illustrating an example aircraft with triboluminescent patch sensors provided thereon, in accordance with embodiments of the disclosure.

Similar to FIG. 1, in FIG. 2, an example transport vehicle 200 in the form of an aircraft 210 with triboluminescent patch sensors 120 embedded therein, in accordance with embodiments of the disclosure, is shown. The triboluminescent patch sensors 120 may be embedded in the regions on the aircraft that may be relatively more prone to mechanical failure. For example, one or more triboluminescent patch sensors 120 may be provided in or around the areas where the aircraft 210 wings are fixed to the aircraft 210 body. In some cases, the triboluminescent patch sensors 120 may be embedded on the surface of the frame and/or body of the aircraft 210. Some of these regions to be monitored may experience relatively higher levels of mechanical stresses and/or fatigue. The triboluminescent patch sensors 120 may be configured to detect one or more emitting conditions associated with the region being monitored around the triboluminescent patch sensors 120. The emitting conditions may be any event that impart a force onto the triboluminescent optical fiber sensors 120.

Other applications of triboluminescent patch sensors 120 may include, but are not limited to, security, transportation infrastructure, transportation vehicles, housing, or the like. For example, embodiments of the disclosure may provide protection of infrastructure, including concrete structures like bridges and dams, from terrorist attacks via impacts and explosion. As another example, bridge owners such as government or private entities may remotely, securely, and efficiently monitor and/or predict the structural integrity of bridges and/or roadways. As yet another example, commercial airline operators may implement real-time monitoring of aircrafts resulting in reduced labor, maintenance cost, and downtime, while providing greater security and safety. Triboluminescent patch sensors 120 may further be used in the aerospace industry to provide real time, distributed monitoring of the structural states of aircrafts, including the structural states of aircrafts following damaging events such as low velocity impact damage.

Figure 3:
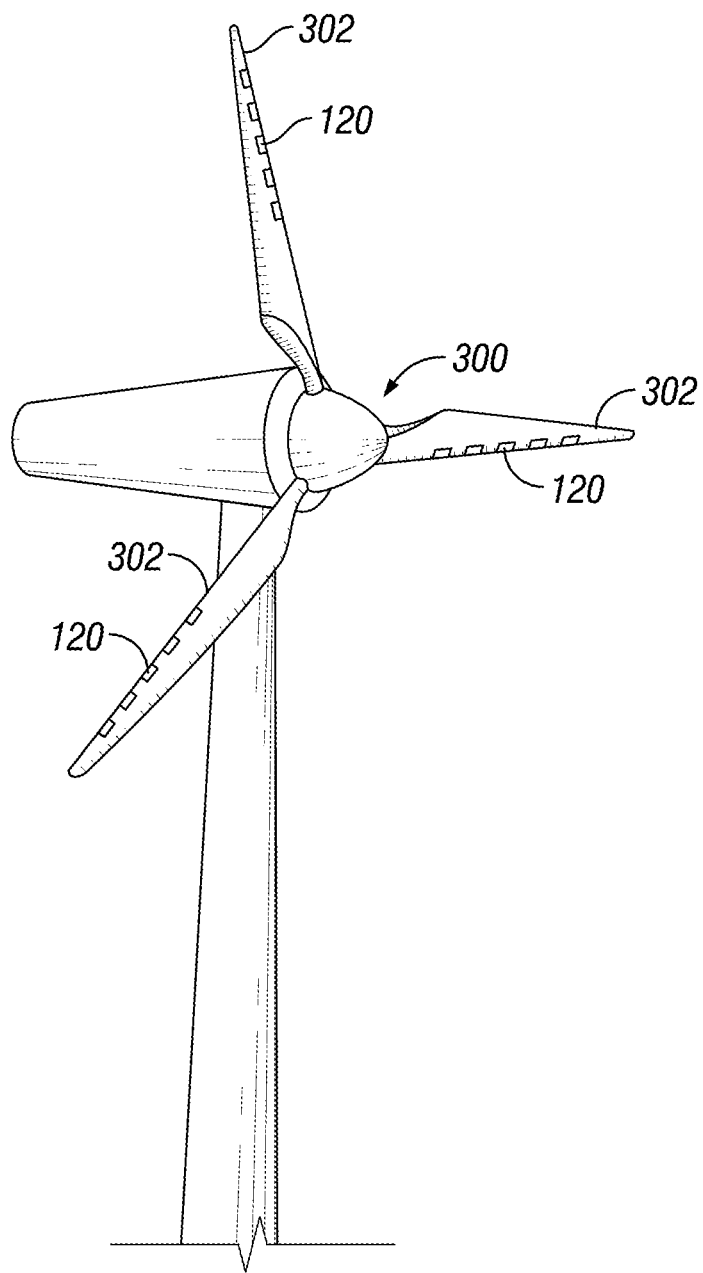
FIG. 3 is a schematic diagram illustrating an example wind turbine blade with triboluminescent patch sensors provided thereon, in accordance with embodiments of the disclosure.

FIG. 3 is a schematic diagram illustrating an example wind turbine blade 302 with triboluminescent patch sensors 120 provided thereon, in accordance with embodiments of the disclosure. Wind turbines 300 with wind blades 302 may experience high levels of shear, as well as compressive and/or tensile stresses. Triboluminescent patch sensors 120 may be deployed onto the blades 302 to monitor the level of stresses and/or strains, impacts, and/or any forces (e.g., bird strikes) being imparted onto the blades 302. In some cases, the monitoring of forces on the blades 302 by the triboluminescent patch sensors 120 may be used to identify critical damage to the blades 302 and/or determine the if the blades 302 are to be replaced and/or repaired. In the same or other cases, the triboluminescent feedback from the triboluminescent patch sensors 120, may provide real time load (e.g., stress/moment) information to a turbine control system for any variety of turbine control, such as controlling the pitching of the wind blades 302.

ITOFPress sensors may be distributed along a wind turbine blade for the purposes of sensing loads along the blade for active control of the turbine. Signals generated at any instrumented section of the blade may be transmitted without any external power source via optical fibers through a hub and to an instrumentation console in a nacelle. The ITOFPress sensors may be flat or curve-shaped. Indeed, in example embodiments, a mix of flat and curved patch sensors 120 may be deployed on a wind turbine to collect load data from various locations, for the purposes of active control, preventive maintenance, and/or damage detection.

Figure 4:
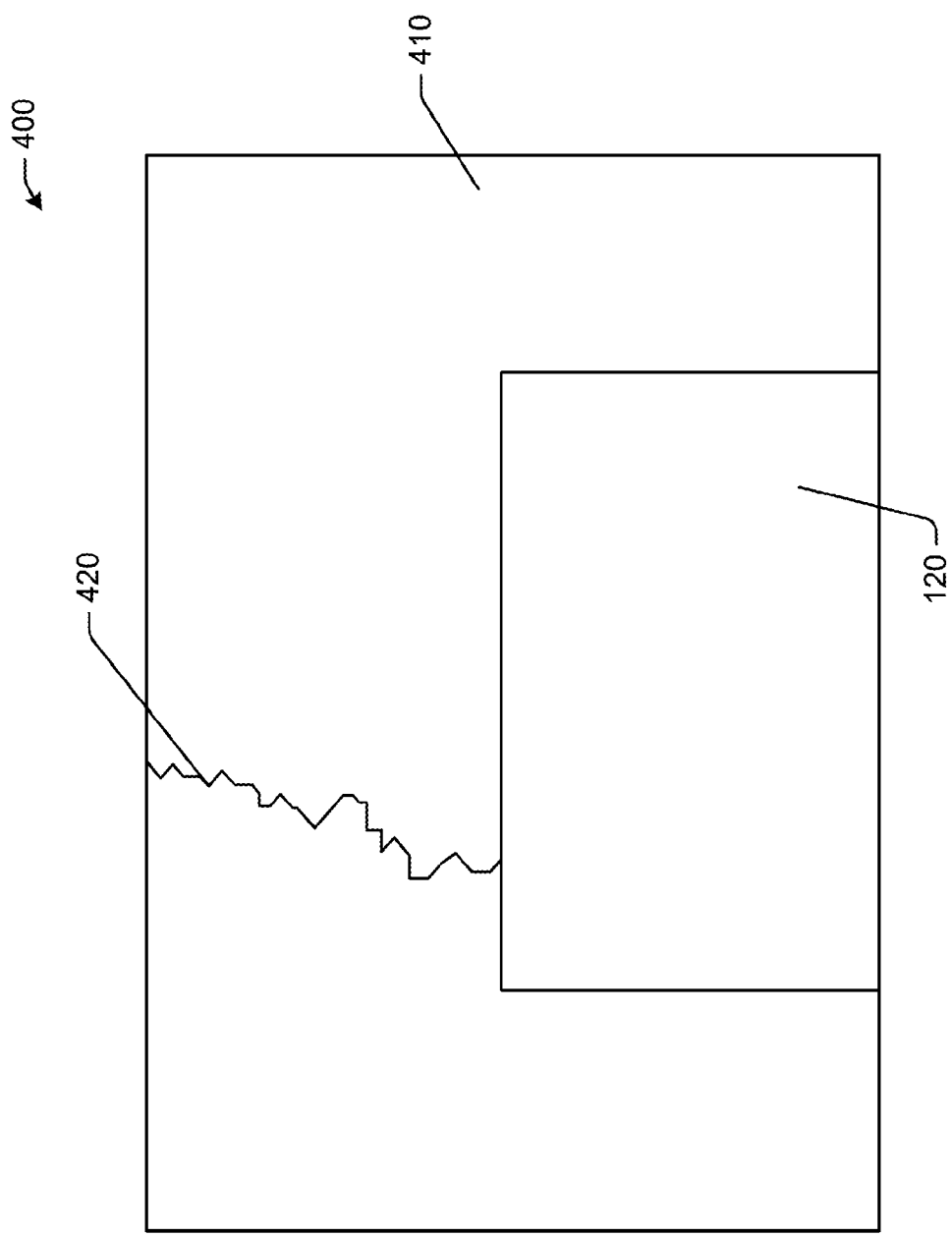
FIG. 4 is a schematic diagram illustrating an example emitting incident in the triboluminescent sensing patch of FIGS. 1-3, in accordance with embodiments of the disclosure.

Referring now to FIG. 4, in an environment 400, a triboluminescent patch sensor 120 is provided on a surrounding material 410 experiencing an emitting condition, in the form of a propagating crack 420 is shown. The surrounding material 410 may be, for example, cement used in the construction of the bridge 110, aluminum used in the construction of the aircraft 210, polymeric material used in the construction of the wind turbine blades 302, or indeed, any suitable material. In this case, the crack 420 may propagate to the triboluminescent patch sensor 120 or in proximity thereof. In other words, in certain embodiments, the triboluminescent patch sensors 120 may be configured to detect damage, such as the crack 420, within the surrounding material 410 without the damage propagating into the triboluminescent patch sensor 120 itself. In other embodiments, the damage to the surrounding material 410 may lead to damage to the triboluminescent patch sensors 120. In either case, for the crack 420 to be detected by the triboluminescent patch sensor 120, the crack 420 may impart forces to the triboluminescent patch sensor 120, such as via an epoxy with which the triboluminescent patch sensor 120 is affixed to the material 410. The triboluminescent patch sensors 120 may be configured to detect when the triboluminescent patch sensors 120 and the triboluminescent materials therein are stressed, pulled apart, ripped, scratched, rubbed and/or fractured. Indeed, the triboluminescent patch sensors 120 may be configured to detect any variety of mechanical force(s) imparted thereon. Therefore, in one aspect, damage to the surrounding material 410 may be detected by utilizing the triboluminescent patch sensor 120. In another aspect, force(s) that may contribute to structural damage of the surrounding material 410 may be detected utilizing the triboluminescent patch sensor 120. Forces imparted to the surrounding material 410 may lead to structural damage to the surrounding material 410 in a relatively catastrophic manner and/or in a manner that may progress over time, such as material fatigue or related processes. In another aspect, the forces may be monitored to provide loading information that may be used to control the structure (e.g., actuation) to prevent overload or enhanced performance in any suitable application, such as in a wind turbine.

It will be appreciated that in certain embodiments, the surrounding material 410 may be subjected to loading and/or unloading of stresses, either or both tensile or compressive, that may lead to fatigue, creep, or other forms of structural damage to the surrounding material 410 over time. The triboluminescent patch sensors 120 in proximity to the surrounding material 410 may be configured to detect these stresses over time and may be configured to provide information related to these stresses to a structural health monitoring system that may track these stresses over time. Indeed, data and/or information from triboluminescent patch sensors 120 may be utilized to make predictions related to crack formation, propagation, and/or structural failure.

Figure 5A:
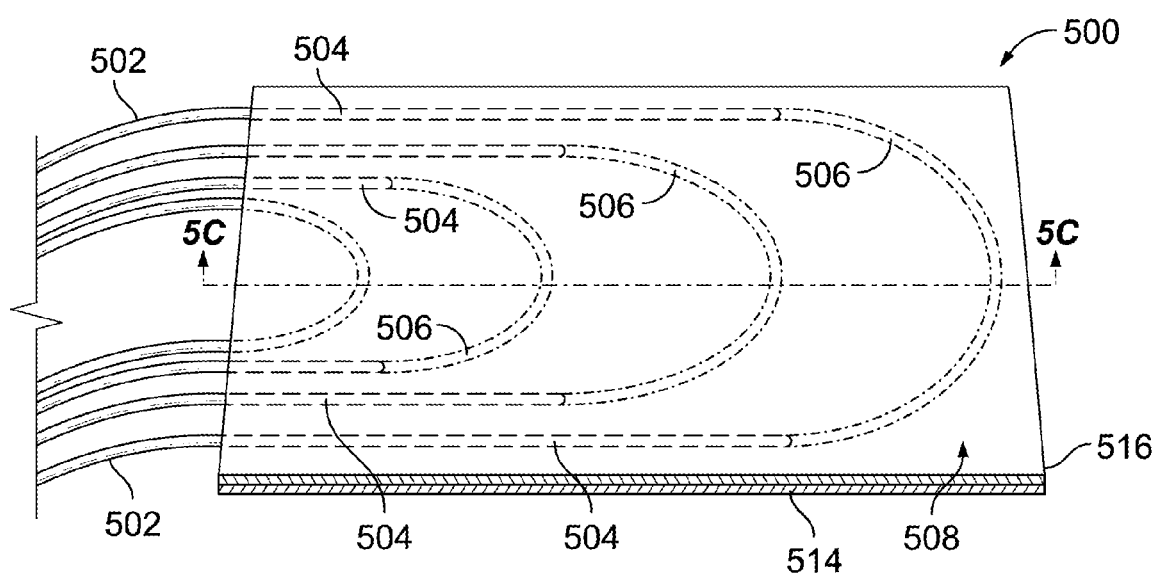
FIG. 5A is a schematic diagram illustrating an example triboluminescent patch sensor, in accordance with embodiments of the disclosure.
Figure 5C:
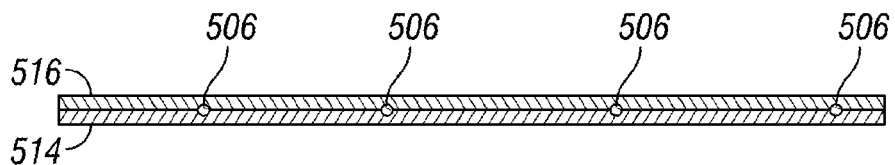
FIG. 5C is a cross-sectional view of the triboluminescent patch sensor of FIG. 5A, taken along the line 5A-5A.
Figure 5B:
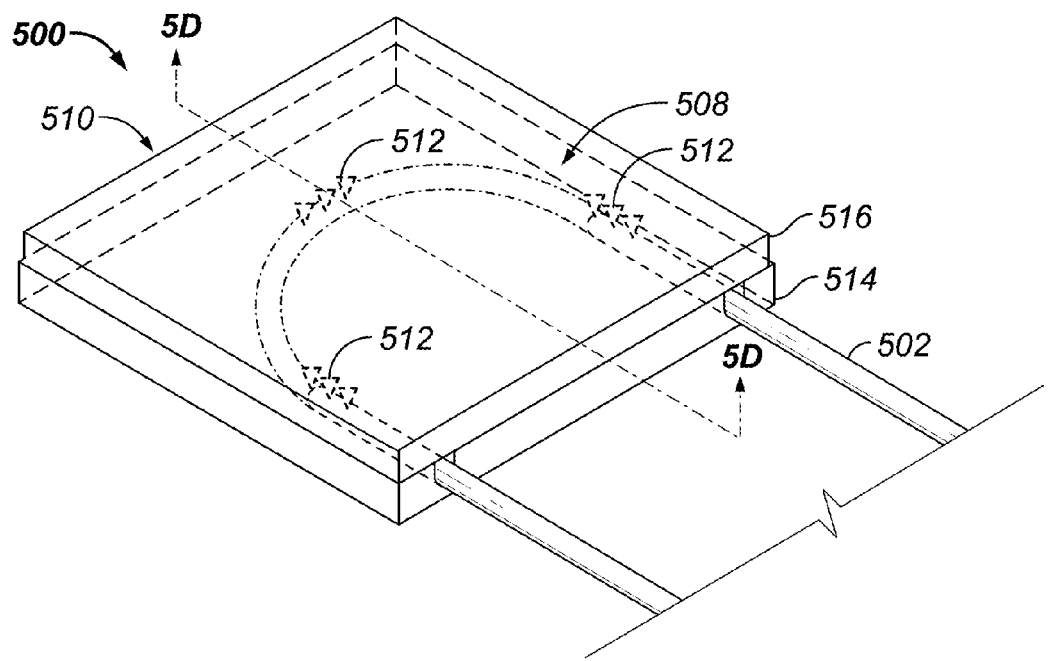
FIG. 5B is a schematic diagram illustrating an example triboluminescent patch sensor, in accordance with embodiments of the disclosure.
Figure 5D:
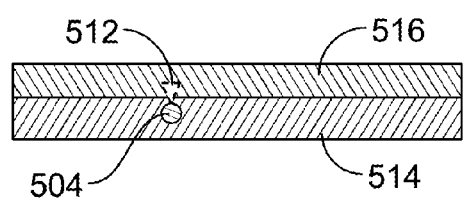
FIG. 5D is a cross-sectional view of the triboluminescent patch sensor of FIG. 5B, taken along the line 5B-5B.

FIGS. 5A-5D are schematic diagrams illustrating example triboluminescent patch sensors 500, in accordance with embodiments of the disclosure. The triboluminescent optical fiber sensor 500 may include one or more optical fibers (OF) 504, such as a polymer optical fiber (POF), with a jacket on portions 502 not embedded within patch 508, and a highly sensitized section 506 that may be coated with triboluminescent material on the fiber 504 and/or the patch 508 in proximity of the fiber 504. The patch 508 has a substrate 514 and an encapsulating cover 516. The optical fibers 504 may be embedded in the patch 508 by being embedded in the substrate 514 as shown in FIG. 5B, or may be embedded in both the substrate and the encapsulating cover, as shown in FIG. 5A.

The optical fiber 504 may be cylindrical in shape, with two ends and a substantially circular shape along its length.

Figure 5E:
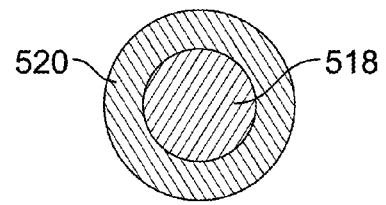
FIG. 5E is a cross-sectional view of an example optical fiber which can be used in the triboluminescent patch sensors depicted in FIGS. 5A-5D.

The optical fiber 504 may be any suitable type of optical fiber 504 including, but not limited to, single mode fiber, multi-mode fiber, POF, glass fiber, silica based fiber, fluorinated glass fiber, coated fiber, or the like. In general, the optical fiber 504 may include a core 518 surrounded by a cladding region 520, as shown in FIG. 5E. The optical fiber 504 may further be configured to accept light at magnitudes and wavelength(s) that may be emitted by the triboluminescent triboluminescent material 506, via the end and/or the sidewalls of the optical fiber 504. The optical fiber 504 may still further be configured to propagate light, such as light at the wavelength(s) emitted by the triboluminescent materials 506, along the length of the optical fiber 504. In one aspect, light may be propagated along the length of the optical fiber 504 due to total internal reflection (TIR) of the lights within the optical fiber 504. Therefore, the refractive indexes selected for the core and the cladding of the optical fiber 504 may be suited, in certain embodiments, for allowing TIR at the wavelength(s) of light emitted by the triboluminescent materials 506. The optical fiber 504 may generally be covered on its outer surface by the jacket at least for a certain portion of the length of the optical fiber 504, such as in the portion 502 that is not embedded within the patch 508. The jacket may be any suitable material including plastics, cloth, paper, or the like, and may be configured to reject any light from entering the optical fiber 504 in those portions 502 of the optical fiber 504 covered by the jacket.

The triboluminescent material 506 may be provided directly on the outer surface of the optical fiber 504 in a portion that is embedded within the patch 508. In certain embodiments, in the construction of the triboluminescent patch sensor 500, the jacket may be removed from a portion of the optical fiber 504 and that portion may be coated with the triboluminescent materials 506 prior to embedding in the patch 508. In other words, the triboluminescent material 506 may be provided by mechanically removing the jacket along a portion of the length of the optical fiber 504, and coating that portion with epoxy containing dispersed triboluminescent materials such as ZnS:Mn crystals prior to embedding within and/or forming the patch 508 thereon. In other example embodiments, the optical fiber 504 may be attached to the patch 508 and TL materials 506 may be coated thereon, such as by dispersing epoxy containing TL materials on the optical fiber 504 and/or portions of the patch 508. There may be any suitable number of triboluminescent material coated optical fiber disposed within the patch sensor. The arrangement of the optical fiber(s) in the patch may be any suitable pattern, such as curved, straight, radial and/or sinusoidal. The construction of the patch may be completed after the dispersing of the TL materials 506 thereon, such as by laminating a cover epoxy sheet onto a base epoxy sheet, where a portion of the optical fiber 504 is held between the top sheet and the base sheet with the Triboluminescent material 506 provided between the top sheet and the base sheet. In this case, the attachment (e.g., lamination, epoxy attach, etc.) of the top sheet and the base sheet may form the patch 508.

The triboluminescent patch sensor 500 may be attached on a structure (e.g., composite structure), as shown in FIGS. 1-3, and can detect damage in the structure by converting mechanical energy resulting from a damage causing event like impacts and crack propagation into triboluminescent (TL) optical signals at the optical fiber 504 and/or patch 508. The triboluminescent material 506, in particular, may be configured to detect mechanical energy/load and/or mechanical damage in surrounding material with which the triboluminescent patch sensor 500 is embedded and generate an optical output and/or signal. In other words, the triboluminescent material 506 of the triboluminescent patch sensor 500 may provide mechano-optical energy conversion that may be utilized in load monitoring as well as the detection of structural damage. The TL signals generated at the triboluminescent patch sensor 500 may then be transmitted through the optical fiber 504 to a photodetector, such as a semiconductor photodetector or photomultiplier tube (PMT) and spectrometer.

As depicted on the patch sensor 510, there may be excitors (e.g., micro-excitors) 512 disposed on and/or in proximity of the optical fiber 504 with TL materials disposed thereon. The micro-excitors 512 may be any suitable material that imparts a sufficient level of friction-induced excitation of the TL materials disposed on or near the optical fiber 504 of the patch sensor 510. As a result, the patch sensor 510 may be configured to emit TL optical emissions from loading events, as sensed by the patch sensor 510, as well as impact events. In other words, a load on a turbine blade may cause deformation of the patch sensor 510 resulting in relative motion between TL-coated optical fiber 504 and micro-excitors 512. The relative motion may result in light emissions (friction-induced) that may be transmitted via the optical fiber 504 to an instrumentation console where the light may be converted to electrical signals for data analysis, interpretation for appropriate action(s), and for storage.

Figure 6A:
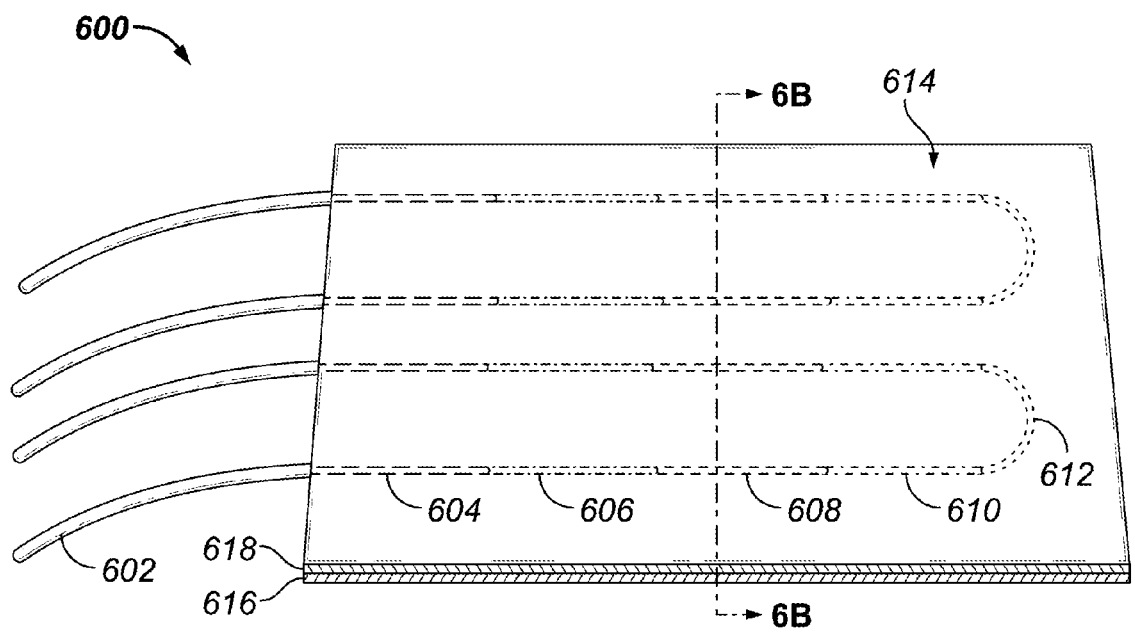
FIG. 6A is a schematic diagram illustrating another example triboluminescent patch sensor, in accordance with embodiments of the disclosure.
Figure 6B:
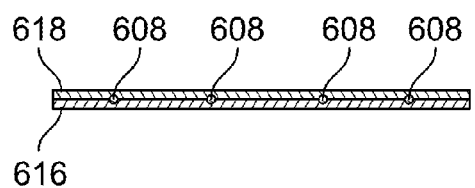
FIG. 6B is a cross-sectional view of the triboluminescent patch sensor of FIG. 6A, taken along the line 6A-6A.

FIGS. 6A and 6B are schematic diagrams illustrating another example triboluminescent patch sensor 600, in accordance with embodiments of the disclosure. In this triboluminescent patch sensor 600, there may be multiple types of TL materials 604, 606, 608, 610, and 612 that are provided on an optical fiber 602 that is partially embedded in a patch 614. The patch 614 may have a substrate 616 and an encapsulating layer 618, so that the optical fiber 602 is embedded in he patch 614 in the substrate 616, in the encapsulating layer 618, both, or is simply positioned between the substrate 616 and the encapsulating layer 618. Although the various TL materials 604, 606, 608, 610, 612 are shown in different portions of the optical fiber 602 embedded within the patch 614 of the triboluminescent patch sensor 600, it will be appreciated that there may be overlaps in the regions of the different TL materials 604, 606, 608, 610, and 612. In some example embodiments, all of the various TL materials may be combined and coated on the optical fiber 602 and/or patch 614 within all TL-sensitive portions of the triboluminescent patch sensor 600. Indeed, the use of different types and/or different concentrations of TL materials 604, 606, 608, 610, and 612 may enable the detection of different types and/or different intensities of TL emitting events.

The TL materials 604, 606, 608, 610, and 612, upon sensing mechanical energy, such as mechanical energy imparted by a damage event in the material on which the triboluminescent patch sensor 600 is deployed, may emit light at one or more characteristic wavelengths or a range of wavelengths. In example embodiments, each of the TL materials 604, 606, 608, 610, and 612 may have a non-overlapping characteristic wavelength and/or range of wavelengths. Thus, the TL material 604, 606, 608, 610, or 612 from which a particular light (e.g., photons) are produced, may be discernable at a detector. Again, there may be micro-excitors disposed on or near the optical fiber 602, to induce frictional transference, concentration, and/or amplification of a loading event and/or mechanical load imparted to the patch sensor 600 from a structure on which the patch sensor 600 may be deployed. The optical fiber 602 may be configured to receive photons generated by the TL materials 604, 606, 608, 610, and 612 from the sides of the optical fiber 602 in the portion on which the TL materials 604, 606, 608, 610, and 612 is provided. The optical fiber 602 may further be configured to guide the light received from the TL materials 604, 606, 608, 610, and 612 down the length of the optical fiber 602. In other words, the wavelengths of light that may be emitted by the TL materials 604, 606, 608, 610, and 612 upon detection of suitable mechanical stimulus, may propagate through the cladding and to the core of the optical fiber 602 and may further exhibit TIR to enable the light to propagate down the length of the optical fiber 602. Therefore, when there may be a suitable loading event damage inducing mechanical event to a structure on which the triboluminescent patch sensor 600 is embedded, the TL materials 604, 606, 608, 610, 612 may emit an optical signal that is indicative of the damage-inducing mechanical event, and at least a portion of that optical signal may propagate to and be transferred by the optical fiber 602. In certain embodiments, the optical fiber 602 may be configured to propagate the optical signal from the TL materials 604, 606, 608, 610, and 612 to a photodetector, such as a semiconductor photodetector or a photomultiplier tube (PMT).

Figure 7:
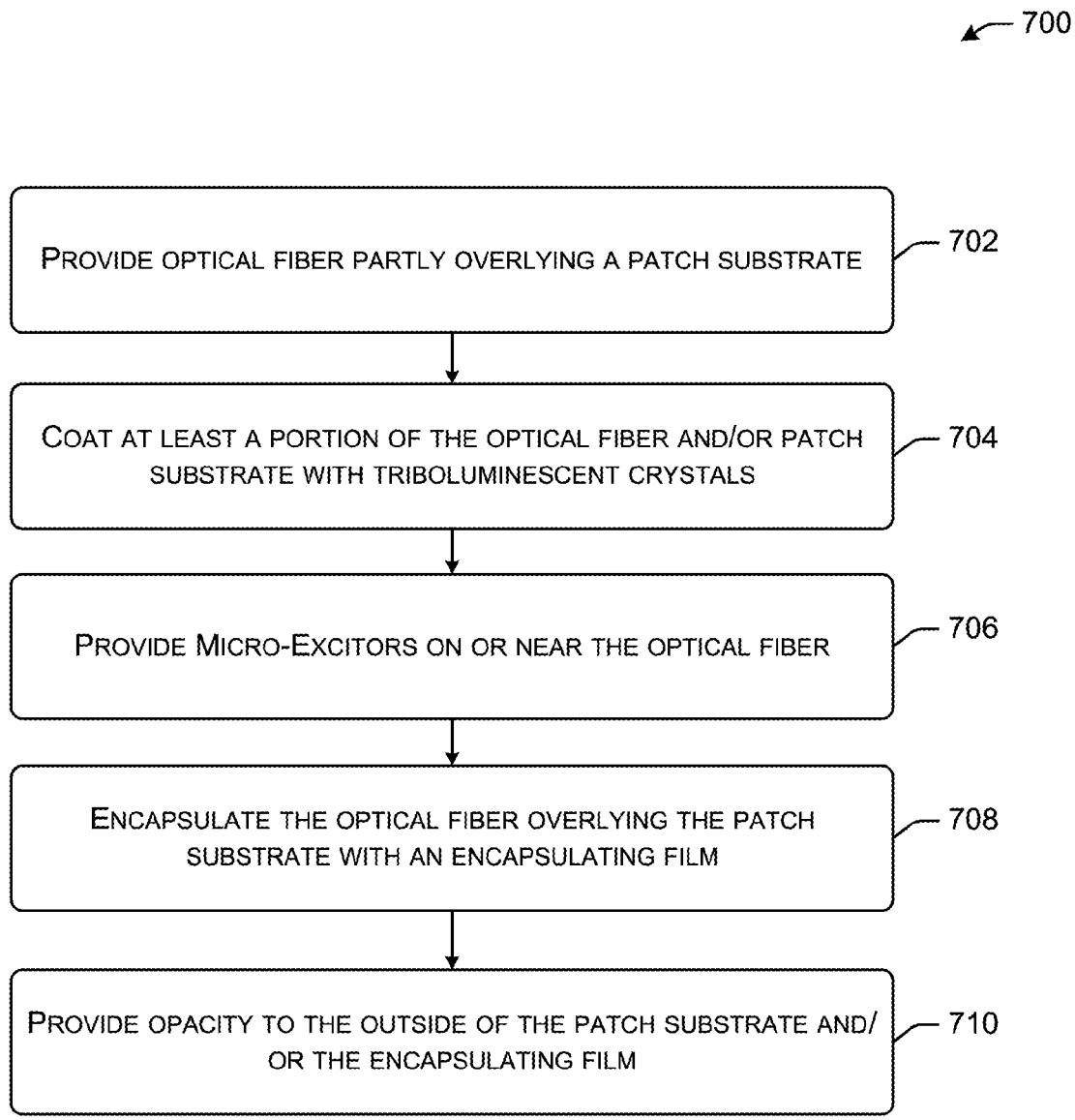
FIG. 7 is a flow diagram depicting an example method of fabricating the triboluminescent patch sensors of FIG. 5 or 6, in accordance with embodiments of the disclosure.

FIG. 7 is a flow diagram depicting an example method of fabricating the triboluminescent patch sensors of FIG. 5 or 6, in accordance with embodiments of the disclosure.

At block 702, an optical fiber may be provided that partially overlaps a patch substrate. In certain embodiments, optical fiber may have a protective jacket thereon through substantially the full length of the optical fiber and the jacket may be removed in a certain portion, such as the portions to be overlying the patch substrate. The jacket may be removed using a variety of suitable mechanisms including, but not limited to, mechanical stripping, chemical dissolving, or the like. The optical fiber may be provided on the patch substrate using any number of mechanisms including, but not limited to, epoxy, glue, tape, mechanical fasteners, and/or any variety of a temporary use of any of the aforementioned mechanisms, combinations thereof, or the like.

At block 704, at least a part of the optical fiber and/or patch substrate may be coated with triboluminescent material, such as a material with triboluminescent crystals disposed within it. The coating with the triboluminescent material contained therein may, in certain embodiments, be an epoxy or UV-cured polymer system with triboluminescent crystals dispersed within the epoxy or UV-cured polymer system. For example, the triboluminescent crystals may be any suitable triboluminescent crystals, such as ZnS:Mn crystals, titanium dioxide ($TiO_2$, which is also commonly referred to as "titania"), zinc oxide (ZnO), magnetite ($Fe_2O_4$), or combinations thereof. In one aspect, the coating on the optical fiber may form the TL material on a portion of the optical fiber that is embedded within the patch. The coating may be provided on the portions of the optical fiber by dipping the optical fiber and/or patch in the epoxy dispersed with triboluminescent materials and allowing the epoxy to dry and/or harden. In some cases, the coated epoxy may be heated to accelerate the drying and/or hardening. In certain other embodiments, the triboluminescent materials may be provided on the optical fiber and/or patch using any suitable process including, but not limited to, chemical vapor deposition (CVD), physical vapor deposition (PVD), evaporative processes, spray processes, or the like. In some cases, various TL materials may be dispersed on the optical fiber and/or patch in separate spray processes.

While the disclosure discusses the use of triboluminescent materials in the coating and in the construct of the TL materials, it will be appreciated that in certain embodiments, other materials, such as fractoluminous, mechanoluminous, and/or piezoluminous materials may be used. The coating may emit radiation when subject to one or more emitting conditions, such as when the triboluminescent material is stressed, pulled apart, ripped, scratched, rubbed, and/or fractured. In some cases, the emitted radiation may be at one or more characteristic wavelength(s) based at least in part on the type of triboluminescent crystals used, stresses imparted to the triboluminescent crystals, the type of polymer matrix-like epoxy in which the triboluminescent crystals are provided, and/or other impurities that may be present in or around the triboluminescent crystals. For example, the triboluminescent crystals used may be a direct bandgap semiconductor material and may have a characteristic wavelength of emissions that is based at least in part on the bandgap of the material.

At block 706, micro-excitors may be provided on or near the optical fiber. The micro-excitors may be any suitable type of abrasive that may be dispersed onto the optical fiber and/or the patch substrate. In some cases, the micro-excitors may be dispersed in a fashion similar to how the TL materials may be provided onto the optical fiber and/or patch substrate. In some alternative embodiments, the micro-excitors may be dispersed onto the patch substrate prior to providing the optical fiber at block 702.

At block 708, the optical fiber may be encapsulated on the patch substrate with an encapsulating film. This may entail, in example embodiments, laminating the patch substrate with the encapsulating film with the optical fiber sandwiched between the patch substrate and the encapsulating film. In some other example embodiments, the optical fiber may be embedded in the patch substrate and the patch substrate may subsequently be cured to harden (e.g., cross-link) the patch substrate with the optical fiber embedded therein. In some example embodiments, the encapsulating film may be the same material type as the patch substrate. In other example embodiments, the encapsulating film may be a different material type than the patch substrate.

At block 708, opacity may be provided to the outside of the patch substrate and/or the encapsulating film. Making the outside of the patch opaque may result in rejecting outside light being collected by the optical fiber that may corrupt the TL-based measurement of tribological events. The outside of the patch may be darkened by using pigments, such as by painting and/or implanting pigments in and/or on the patch substrate and/or the encapsulating film. In some cases, a thermal and/or UV treatment may lead to a darkening of the outside of the patch.

It will be understood that the triboluminescent patch sensor may be coupled to a photodetector. The coupling may enable the optical fiber to guide the TL signal generated to the photodetector. The photodetector may be any suitable device that converts an optical signal provided thereon to a corresponding electrical signal. The photodetector may include any variety of photodiode, photomultiplier tubes, photovoltaic cells, photoresistors, phototransistors, or the like. In certain embodiments, multi-pixel photodetectors, such as charge coupled devices (CCDs) and/or image sensors may be used. The photodetector may, in certain embodiments, be sensitive to one or more optical wavelength(s) that may be emitted by the TL materials provided on the OF and/or patch of the triboluminescent patch sensor.

In example embodiments, the photodetector may be coupled to a computing device configured to receive and interpret a signal from the photodetector. The computing device may be any device configured to receive the signal from the photodetector and may include any variety of computing devices including, but not limited to, servers, desktop computers, notebook computers, netbook computers, tablet computing devices, pad computing devices, personal digital assistants (PDAs), smart phones, digital readers, or combinations thereof. The computing device may have instructions, applications, and/or software running thereon that may enable the computing device to analyze signals received form the photodetector to provide an indication of events sensed by the triboluminescent patch sensor 120.

It should be noted that the method 700 may be modified in various ways in accordance with certain embodiments. For example, one or more operations of the method 700 may be eliminated or executed out of order in other embodiments. Additionally, other operations may be added to the method 700 in accordance with other embodiments.

Figure 8:
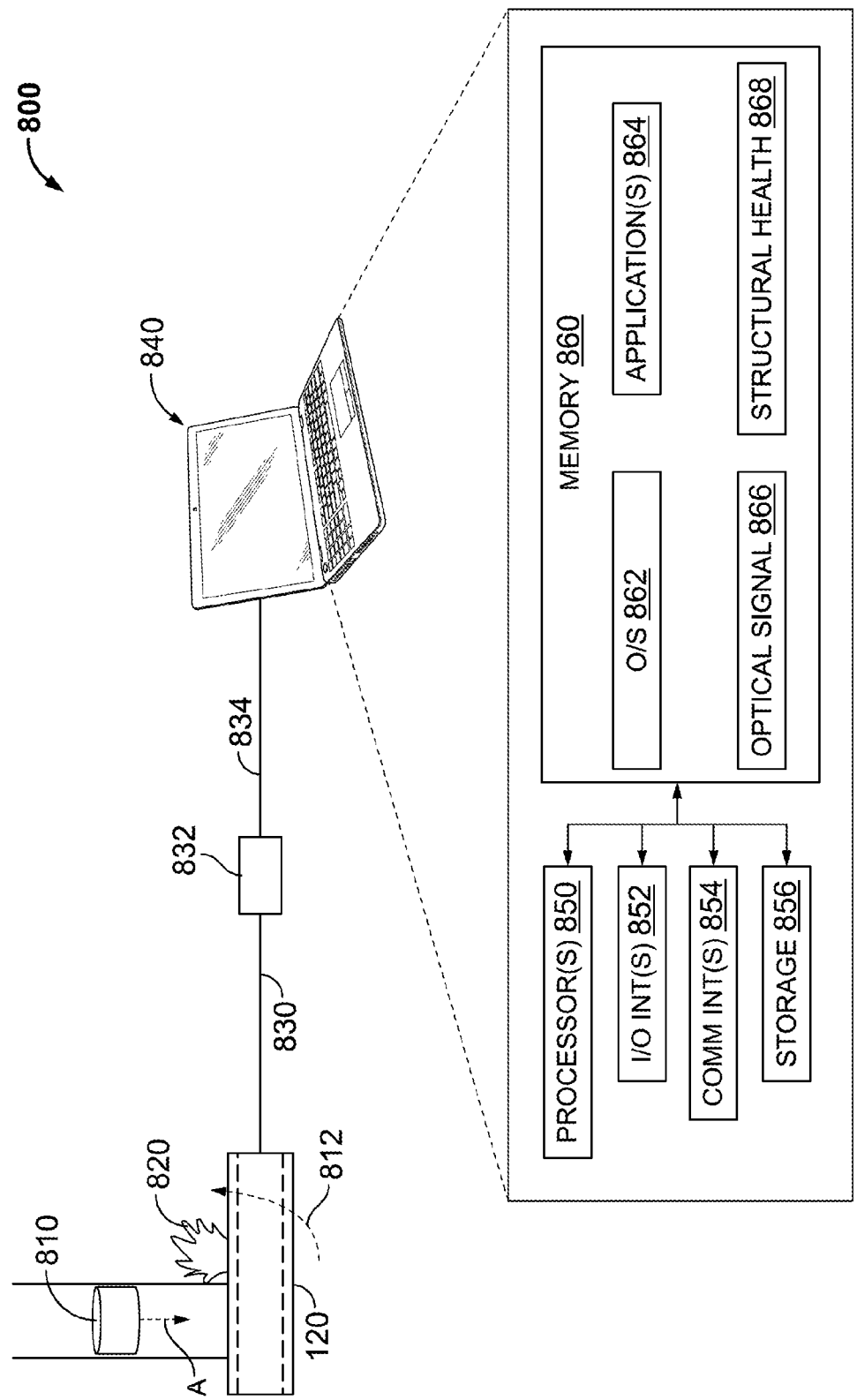
FIG. 8 is a schematic diagram illustrating an example of a system for monitoring load and structural health incorporating the triboluminescent patch sensor of FIG. 5 or 6, in accordance with embodiments of the disclosure.

FIG. 8 is a schematic diagram illustrating an example structural health monitoring system 800 incorporating a triboluminescent patch sensor 120. The triboluminescent patch sensor 120 may be a sensor according to any embodiment, for example the sensors 500, 600 of FIG. 5 or 6, in accordance with embodiments of the disclosure. The structural health monitoring system 800 may include the triboluminescent patch sensor 120 coupled to a photodetector 832 via optical fiber 830, and may be further coupled to a computing device 840 via electrical connection 834. The triboluminescent patch sensor 120 is depicted as sensing an emitting event in the form of an impact by a weight 810 falling in direction A and/or a loading on the patch sensor 120. Although an impact event is depicted here, it will be appreciated that the triboluminescent patch sensor 120 may be able to detect any suitable mechanical event, such as stressing, being pulled apart, ripping, scratching, rubbing and/or fracturing. Furthermore, although a shear and/or bending of the patch sensor 120 in direction 812 is depicted, it will be appreciated that any suitable type of loading, such as compressive and/or tensile, may result in an emitting event 820. The impact may result in an optical emission 820 from the TL material(s) of the triboluminescent patch sensor 120, part of which may propagate to the core of the optical fiber and may further be transmitted to the photodetector via the optical fiber. It will be appreciated that the photodetector may be any suitable optical detection device including photomultiplier tubes, photovoltaic cells, photoresistors, phototransistors, charge coupled devices, image sensors, or the like.

The computing device 840 of the structural health monitoring system 800 may be any suitable device including servers, desktop computers, notebook computers, netbook computers, tablet computing devices, pad computing devices, personal digital assistants (PDAs), smart phones, digital readers, or combinations thereof. The computing device 840 may include one or more processors 850, one or more input output (I/O) interfaces 852, one or more communications interfaces 854, one or more storage devices 856, and one or more memories 860. It will be appreciated that the computing device 840 may include other components or elements that enable the computing device 840 to perform the methods and processes described herein in accordance with embodiments of the disclosure.

The one or more processors 850 may be configured to execute and/or operate one or more instructions, applications, and/or software stored in the memory 860 of the computing device 840 to provide structural health monitoring functionality. The processors 850 may further be configured to receive input from or provide output to user interfaces of the computing device 840. In some examples, the one or more processors 850 of the computing device 840 may be implemented as appropriate in hardware, software, firmware, or combinations thereof. Software or firmware implementations of the one or more processors 850 may include computer-executable or machine-executable instructions written in any suitable programming language to perform the various functions described. Hardware implementations of the processors 850 may be configured to execute computer-executable or machine-executable instructions to perform the various functions described. The one or more processors 850 may include without limitation, a central processing unit (CPU), a digital signal processor (DSP), a reduced instruction set computer (RISC), a complex instruction set computer (CISC), a microprocessor, a microcontroller, a field programmable gate array (FPGA), or any combination thereof. The computing device 840 may also include a chipset (not shown) for controlling communications between the one or more processors 850 and one or more of the other components of the computing device 840. The one or more processors 850 may also include one or more application specific integrated circuits (ASICs) or application specific standard products (ASSPs) for handling specific data processing functions or tasks.

The memory 860 may include one or more volatile and/or non-volatile memory devices including, but not limited to, random access memory (RAM), dynamic RAM (DRAM), static RAM (SRAM), synchronous dynamic RAM (SDRAM), double data rate (DDR) SDRAM (DDR-SDRAM), RAM-BUS DRAM (RDRAM), flash memory devices, electrically erasable programmable read only memory (EEPROM), non-volatile RAM (NVRAM), universal serial bus (USB) removable memory, or combinations thereof. The memory 860 may store program instructions that are loadable and executable on the processor(s) 850, as well as data generated or received during the execution of these programs.

Turning to the contents of the memory 860 in more detail, the memory 860 may include an operating system (O/S) 862, applications 864, an optical signal module 866, and/or a structural health module 868. Each of the modules and/or software may provide functionality for the computing device 840, when executed by the processors 850. The modules and/or the software may or may not correspond to physical locations and/or addresses in memory 860. In other words, the contents of each of the modules may not be segregated from each other and may, in fact, be stored in at least partially interleaved positions on the memory 860.

The O/S 862 may have one or more operating systems stored thereon. The processors 850 may be configured to access and execute one or more of the O/S 862 to operate the system functions of the computing device 840. System functions, as managed by the O/S 862, may include memory management, processor resource management, driver management, application software management, system configuration, and the like. The O/S may be any variety of suitable operating systems including, but not limited to, Google® Android®, Microsoft® Windows®, Microsoft® Windows® Server®, Linux, Apple® OS-X®, Apple® iOS®, or the like. The O/S 862 may further be utilized in structural health assessment and monitoring. In other words, the O/S 862 may be the framework under which the structural health monitoring system 800 may interact with users of the structural health monitoring system 800.

The applications module 864 may have one or more software applications stored thereon that may be accessed and executed by the processors 850 to provide the computing device 840 functionality and services. The one or more applications 864 may be run on the computing device 840 to process files and data locally on the computing device 840 or remotely from the computing device 840. The applications of the application module 864 may include any suitable applications, such as computational software, word processing software, database software, or the like. In certain embodiments, the applications module 864 may include one or more applications for determining the structural health of one or more structures, based on inputs from one or more photodetectors.

The optical signal module 866 may have stored thereon instructions and/or applications that when executed by processors 850, may provide various functionality associated with analyzing the output signal of the photodetector. The photodetector signal may be an electrical signal associated with the optical output 820 of the triboluminescent patch sensor 120 produced in response to a mechanical event detected by the triboluminescent patch sensor 120. The computing device 840 may be configured to receive the electrical signal from the photodetector and determine the type of mechanical event that produced the signal. In other words, the processors 850, based at least in part on one or more models and/or algorithms, may be able to ascertain the nature of damage and/or mechanical event imparted on the structure on which the triboluminescent patch sensor 120 is monitoring. Additionally, the processors 850 may be able to assess the magnitude of a detected mechanical event (e.g., loading) on the structure on which the triboluminescent patch sensor 120 is monitoring. In certain embodiments, the instructions stored in the optical signal module 866 may enable the computing device 840 and the processors 850 thereon to store a log and/or a time series of mechanical events detected using the triboluminescent patch sensor 120. For example, a time series of mechanical events with predicted type of event, such as a crack propagation or flexing, as well as the magnitude of the mechanical event, may be stored. This information may be stored in the memory 860 or other suitable storage location, such as an external storage device or on the cloud. In certain embodiments, the information may be communicated by the computing device 840 via one or more networks and/or communicative links to an external server or other entity.

The structural health monitoring module 868 may have instructions and/or applications stored therein that when executed by the processors 850, the computing device 840 may be configured to analyze the signals produced by the triboluminescent patch sensor 120 and received by the computing device 840 via the photodetector. In one aspect, the processors 850 may be configured to analyze one or more signals indicative of mechanical event and predict a probability of structural failure or the failure of a component of the monitored structure. The structural health monitoring module may include models and/or algorithms that may identified in predicting the failure of structural components that are being monitored. For example, the processors 850 may consider time series signals over a relatively long period of time, from the triboluminescent optical fiber sensor 120 and predict a probability of fatigue related failure of an associated structure or a portion thereof. In certain embodiments, the health monitoring module 868 may provide a user of the structural health monitoring system 800 with an indication of the structural health of a monitored structure. For example, the processors 850 may display one or more received triboluminescent patch sensor 120 signals on an output component, such as a display screen, of the computing device 840. Additionally, the processors 850 may provide one or more alarms if a mechanical event of a relatively high magnitude is detected or if the structural health monitoring system 800 determines that the risk of structural failure of a monitored structure or a portion thereof is greater than a predetermined threshold level.

It will be appreciated that there may be overlap in the functionality of the instructions stored in the O/S module 862, applications module 864, optical signal module 866, and the structural health module 868. In fact, the functions of the four aforementioned modules 862, 864, 866, and 868 may interact and cooperate seamlessly under the framework of the computing device 840. Indeed, each of the functions described for any of the modules 862, 864, 866, and 868 may be stored in any other module 862, 864, 866, and 868 in accordance with certain embodiments of the disclosure. Further, in certain embodiments, there may be one single module that includes the instructions, programs, and/or applications described within the O/S module 862, applications module 864, optical signal module 866, and the structural health module 868.

It will be appreciated that while a physical communicative link 834 is depicted between the photodetector 832 and the computing device 840, there may be any suitable communicative link. For example, there may be a wireless link between the photodetector and the computing device 840 in certain embodiments of the disclosure. Furthermore, it will be appreciated that the computing device 840 may receive signals from more than one photodetector and/or associated triboluminescent optical fiber sensors 120. For example, a bridge 110 may have multiple triboluminescent patch sensors 120 embedded therein and a single computing device 840 may monitor all of the triboluminescent patch sensors 120 associated with that particular bridge 110. Further still, a single computing device 840 may be used to monitor multiple monitored structures each with one or more triboluminescent patch sensors 120 embedded therein or provided thereon.

Figure 9:
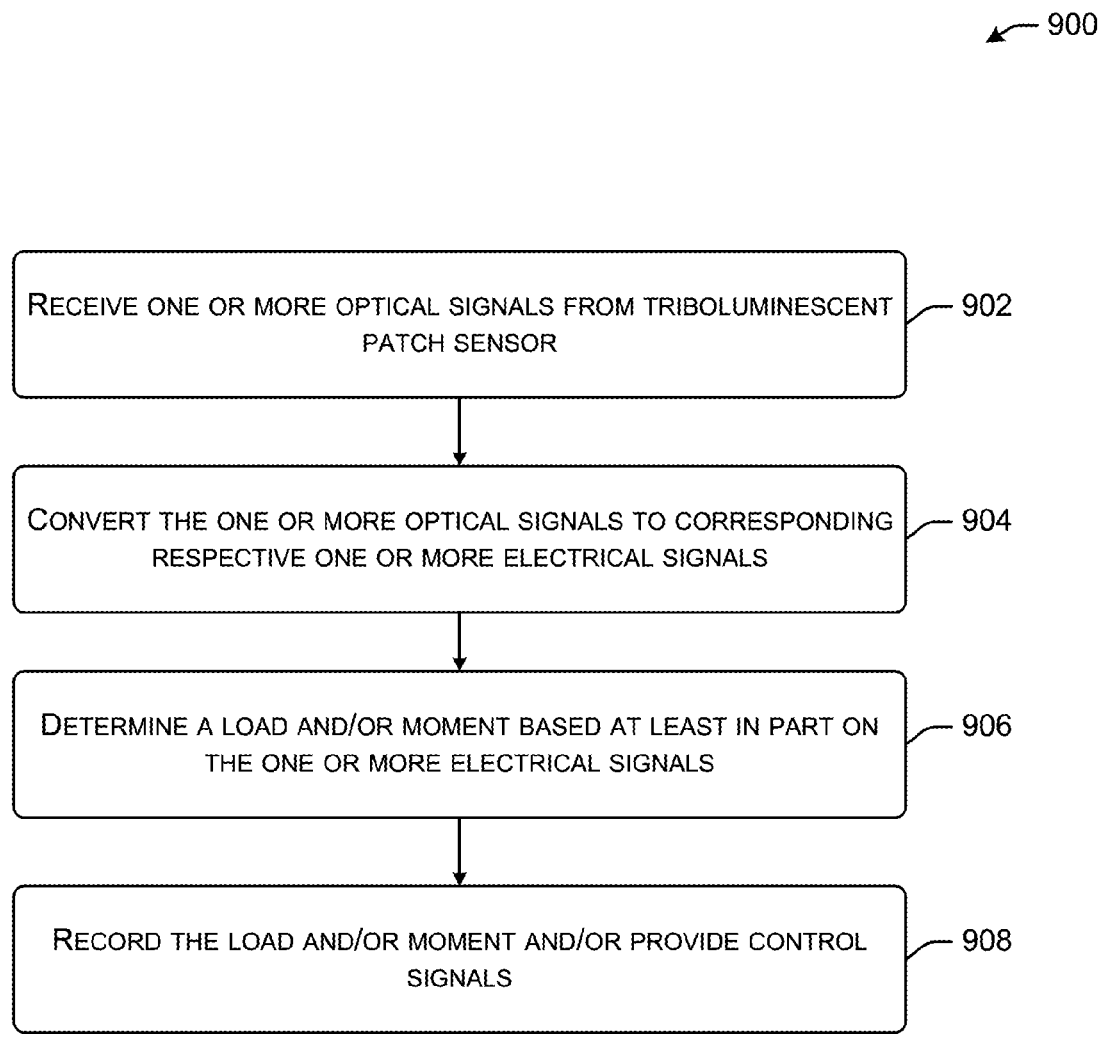
FIG. 9 is a flow diagram depicting an example method of real time monitoring of load and structural health using the example monitoring system of FIG. 8, in accordance with embodiments of the disclosure.

FIG. 9 is a flow diagram depicting an example method 900 of providing load and/or structural health monitoring using the example system 800 of FIG. 8, in accordance with embodiments of the disclosure. At block 902, one or more optical signals may be received from the triboluminescent patch sensor 120. As discussed above, the one or more optical signals may be indicative of mechanical energy being imparted to the triboluminescent patch sensor 120 from material surrounding and/or in proximity of the triboluminescent patch sensor 120. In some cases, the signal may also be indicative of damage to the triboluminescent patch sensor 120. In other cases, the signal may not be indicative of damage to the triboluminescent patch sensor 120. In addition, in certain embodiments the signal may be indicative of damage to the structure being monitored by the triboluminescent patch sensor 120. In other cases, the signal may be indicative of stressing of the structure being monitored and this load information may serve as inputs into a control system for better controlling of the structure being monitored to protect from damage or to enhance performance (e.g. wind turbine control system). This stressing of the monitored structure may, over time, lead to the degradation of the structural integrity of the monitored structure. In yet other cases, the detected signal may be of a type and/or magnitude that may not be indicative of critical damage or fatigue of the monitored structure. It will be appreciated that the one or more signals generated by the triboluminescent patch sensor 120 in response to a mechanical event may be generated at the TL materials of the triboluminescent patch sensor 120.

At block 904, the one or more optical signals may be converted to corresponding respective one or more electrical signals. As described in conjunction with FIG. 8, a photodetector, such as a photodiode, may be used to convert the one or more optical signals to corresponding respective one or more electrical signals. In some cases, the electrical signals may have different levels of noise and/or signal integrity compared to the corresponding respective optical signals. These differences may, in certain cases, be a result of bandwidth limitations of the photodetector and/or noise associated with optical-to-electrical signal conversion. In some cases, the conversion may lead to some rounding and/or ringing of the electrical signals compared to the corresponding optical signals.

At block 906, a load and/or moment may be determined based on the one or more electrical signal. The load and/or moment may be determined from any variety of properties of the one or more electrical signals, such as for example magnitude, frequency, etc.

At block 908, the load and/or moment may be recorded (e.g., stored). Optionally, for control systems a control signal may be generated and provided to an actuator or other mechanical device. For example, in the case of the wind turbine, control signals may be generated to control the blades of the wind turbine.

While certain embodiments of the disclosure have been described in the disclosed embodiments, it is to be understood that the invention is not to be limited to the disclosed embodiments, but on the contrary, is intended to cover various modifications and equivalent arrangements included within the scope of the appended claims. Although specific terms are employed herein, they are used in a generic and descriptive sense only and not for purposes of limitation.

This written description uses examples to disclose certain embodiments of the invention, including the best mode, and also to enable any person skilled in the art to practice certain embodiments of the invention, including making and using any devices or systems and performing any incorporated methods. The patentable scope of certain embodiments of the invention is defined in the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

Embodiments may be provided as a computer program product including a non-transitory machine-readable storage medium having stored thereon instructions (in compressed or uncompressed form) that may be used to program a computer (or other electronic device) to perform processes or methods described herein. The machine-readable storage medium may include, but is not limited to, hard drives, floppy diskettes, optical disks, CD-ROMs, DVDs, read-only memories (ROMs), random access memories (RAMs), EPROMs, EEPROMs, flash memory, magnetic or optical cards, solid-state memory devices, or other types of media/machine-readable medium suitable for storing electronic instructions. Further, embodiments may also be provided as a computer program product including a transitory machine-readable signal (in compressed or uncompressed form). Examples of machine-readable signals, whether modulated using a carrier or not, include, but are not limited to, signals that a computer system or machine hosting or running a computer program can be configured to access, including signals downloaded through the Internet or other networks. For example, the distribution of software may be an Internet download.

Although embodiments have been described in language specific to structural features and/or methodological acts, it is to be understood that the disclosure is not necessarily limited to the specific features or acts described. Rather, the specific features and acts are disclosed as illustrative forms of implementing the embodiments. Conditional language, such as, among others, "can," "could," "might," or "may," unless specifically stated otherwise, or otherwise understood within the context as used, is generally intended to convey that certain embodiments could include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

We claim:

1. A sensing patch comprising:
    a substrate having a first side and a second side opposing the first side;
    an optical fiber comprising an outer surface, wherein at least a portion of the optical fiber is at least partially embedded within the substrate;
    a triboluminescent material provided on at least a portion of the outer surface of the optical fiber;
    micro-excitors provided on at least a portion of the outer surface of the optical fiber; and
    an encapsulating cover having a first side and a second side opposing the first side, wherein the first side of the encapsulating cover is attached to the second side of the substrate,
    wherein the triboluminescent material is configured to provide an optical emission when subjected to an emitting condition, and wherein the optical fiber is configured to receive and transmit at least a portion of the optical emission.

2. The sensing patch of claim 1, wherein the optical fiber is at least one of: (i) a polymer optical fiber; (ii) a glass-based optical fiber; (iii) a single mode optical fiber; or (iv) a multi-mode optical fiber.

3. The sensing patch of claim 1, further comprising jacket disposed over at least a segment of the optical fiber not embedded within the patch.

4. The sensing patch of claim 1, wherein the triboluminescent material comprises at least one of: (i) an epoxy, or (ii) an ultraviolet (UV)-cured polymer system with triboluminescent crystals dispersed therein.

5. The sensing patch of claim 4, wherein the triboluminescent crystals comprise ZnS:Mn crystals.

6. The sensing patch of claim 1, wherein the emitting condition arises when the triboluminescent material is at least one of: (i) stressed; (ii) pulled apart; (iii) ripped; (iv) scratched; (v) rubbed; or (vi) fractured.

7. The sensing patch of claim 1, wherein the first side of the substrate and the second side of the encapsulating cover are opaque to a characteristic wavelength of the triboluminescent material.

8. A system comprising:
    a photodetector; and
    a sensing patch optically coupled to the photodetector, wherein the sensing patch comprises:

a substrate having a first side and a second side opposing the first side;
an optical fiber comprising an outer surface, wherein at least a portion of the optical fiber is at least partially embedded within the substrate;
a triboluminescent material provided on at least a portion of the outer surface of the optical fiber;
micro-excitors provided on at least a portion of the outer surface of the optical fiber; and
an encapsulating cover having a first side and a second side opposing the first side, wherein the first side of the encapsulating cover is attached to the second side of the substrate,
wherein the triboluminescent material is configured to provide an optical emission when subjected to an emitting condition, and wherein the optical fiber is configured to receive at least a portion of the optical emission and transmit the at least the portion of the optical emission to the photodetector.

9. The system of claim 8, wherein the optical fiber is at least one of: (i) a polymer optical fiber; (ii) a glass-based optical fiber; (iii) a single mode optical fiber; or (iv) a multi-mode optical fiber.

10. The system of claim 8, further comprising jacket disposed over at least a segment of the optical fiber not embedded in the patch.

11. The system of claim 8, wherein the triboluminescent material comprises a polymer system with triboluminescent crystals dispersed therein.

12. The system of claim 11, wherein the triboluminescent crystals comprise ZnS:Mn crystals.

13. The system of claim 8, wherein the emitting condition arises when the triboluminescent material is at least one of: (i) stressed; (ii) pulled apart; (iii) ripped; (iv) scratched; (v) rubbed; or (vi) fractured.

14. The system of claim 8, further comprising at least one processor coupled to the photodetector and configured to run software and to determine an occurrence of the emitting condition.

15. A method of forming a sensing patch comprising:
providing a substrate having a first side and a second side opposed to the first side;
attaching a portion of an optical fiber comprising an outer surface to the second side of the substrate;
applying a triboluminescent material on at least a portion of the outer surface of the portion of the optical fiber;
applying micro-excitors on at least a portion of the outer surface of the portion of the optical fiber; and
applying an encapsulating cover having a first side and a second side opposing the first side, such that the first side of the encapsulating cover is attached to the second side of the substrate,
wherein the triboluminescent material is configured to provide an optical emission when subjected to an emitting condition, and wherein the optical fiber is configured to receive and transmit at least a portion of the optical emission.

16. The method of claim 15, further comprising optically coupling the optical fiber to at least one photodetector.

17. The method of claim 15, wherein the optical fiber is at least one of: (i) a polymer optical fiber; (ii) a glass-based optical fiber; (iii) a single mode optical fiber; or (iv) a multi-mode optical fiber.

18. The method of claim 15, wherein the triboluminescent material is at least one of: (i) an epoxy or (ii) an ultraviolet (UV)-cured polymer system dispersed with triboluminescent crystals.

19. The method of claim 18, wherein the triboluminescent crystals comprise ZnS:Mn crystals.

20. The method of claim 15, wherein an emitting condition arises when the triboluminescent material is at least one of: (i) stressed; (ii) pulled apart; (iii) ripped; (iv) scratched; (v) rubbed; or (vi) fractured.

* * * * *